United States Patent
Morten

(10) Patent No.: US 6,316,196 B1
(45) Date of Patent: Nov. 13, 2001

(54) METHODS FOR ANALYZING LTC4 SYNTHASE POLYMORPHISMS AND DIAGNOSTIC USE

(75) Inventor: John Edward Norris Morten, Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/485,636

(22) PCT Filed: Aug. 18, 1998

(86) PCT No.: PCT/GB98/02468

§ 371 Date: Feb. 15, 2000

§ 102(e) Date: Feb. 15, 2000

(87) PCT Pub. No.: WO99/10529

PCT Pub. Date: Mar. 4, 1999

(30) Foreign Application Priority Data

Aug. 22, 1997 (GB) .................................................. 9717766

(51) Int. Cl.$^7$ .............................. C12Q 1/68; C12P 19/34; C07H 21/04

(52) U.S. Cl. .............................. 435/6; 435/91.2; 435/810; 536/23.1; 536/23.5; 536/24.31; 536/24.33; 536/23.4

(58) Field of Search .............................. 435/6, 91.2, 810; 536/23.1, 23.5, 24.31, 24.33, 23.4

(56) References Cited

FOREIGN PATENT DOCUMENTS

| | | |
|---|---|---|
| 93/18178 | 9/1993 | (WO) . |
| WO 93/25668 | 12/1993 | (WO) . |
| 95/32280 | 11/1995 | (WO) . |
| 95/33839 | 12/1995 | (WO) . |
| WO 97/42347 | 11/1997 | (WO) . |

OTHER PUBLICATIONS

Cowburn et al.; "Overexpression of Leukotriene $C_4$ Synthase in Bronchial Biopsies from Patents with Aspirin–intolerant Asthma", J. Clin. Invest., vol. 101, 1998, pp. 834–846.

Holgate; "Biomarkers of asthma"; Commentary, The Lancet, vol. 351, May, 1998, pp. 1300–1301.

Horwitz et al.; "The Role of Leukotriene Modifiers in the Treatment of Asthma"; Am J Respir Crit Care Med, vol. 157, 1998, pp. 1363–1371.

Szczeklik, "Mechanism of aspirin–induced asthma"; Allergy, vol. 52, 1997, pp. 613–619.

Tan, "The role of antileukotrienes in asthma management"; Asthma, 1998, pp. 25–30.

Busse W W: "The role of leukotrienes in astma and allergic rhinitis" Clinical and Experimental Allergy, vol. 26, 1996, pp. 868–879.

Penrose J F Et Al: "Molecular cloning of the gene for human leukotriene C4 synthase" Journal of Biological Chemistry, vol. 271, No. 19, 1996, pp. 11356–11361.

Welsch D J Et Al: "Molecular Cloning and Expression of Human Leukotriene–C4 Synthase" Proceedings of the National Academy of Sciences of USA, vol. 91, Oct. 1994, pp. 9745–9749.

Newton C R Et Al: Analysis of any point mutation in DNA. The amplification refractory mutation system (arms) Nucleic acids research, vol. 17, No. 7, Apr. 11, 1989, pp. 2503–2516.

Sanak M Et Al: "Leukotriene C4 synthase promoter polymorphism and risk of aspirin–induced asthma" The Lancet, vol. 350, 1997, pp. 1599–1600.

*Primary Examiner*—Carla J. Myers
(74) *Attorney, Agent, or Firm*—Pillsbury Winthrop LLP

(57) ABSTRACT

This invention relates to single nucleotide polymorphisms in the $LTC_4$ synthase gene, EMBL accession no. U50136, particularly at one or more of positions 375, 815, 1003, 2169 and 2742. The invention also relates to methods and materials for analyzing allelic variation in the $LTC_4$ synthase gene, and to the use of $LTC_4$ synthase polymorphism in tie diagnosis and treatment of leukotriene mediated diseases such as asthma and allergic rhinitis.

12 Claims, No Drawings

SEQUENCE LISTING (1) GENERAL INFORMATION:

(iii) NUMBER OF SEQUENCES: 26

(2) INFORMATION FOR SEQ ID NO: 1:

(i) SEQUENCE CHARACTERISTICS:
      (A) LENGTH: 4465 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
GAGCTCACAG AGCCCCCAGC TGGGGCATAT CTGGTTTCCG GGGGCAGGGG CGATACCCAG      60

AGGAGGAAGA AGGGATTCTG AGAGAGCCCA ACAGGCTCCG AGCCTCAGGC TGGAGCTGAG     120

CTTGGGGCAG CAAGGAAGGA CCAGGTGCGA GGGCAGAACC ATGCGGCCCG ACCCCTGCAG     180

CACGGCCTGT GGCCTCCCCC AGCTCCTGCC CGTGCTTCTG GGTCAGTCTG GACTTTGCCA     240
```

-continued

```
CTTCTGACCA AAAGCCACCG CAAACCCACT CAAGCCAAAA GAGGAAGTGA CCGTTAGGCC    300

CAACTGGGAA GGCTGGCGGC CAGGGGCACT CCAGGCAGGG CGAGGGGGGC GGCCGGGGGC    360

GCTCCAGGCG GGGCGAGGGA GACACCCAGA ACTCCAGGCA GGAGTCCTCG GGTGCCACCT    420

TTCCTCTCCA CCTGGCCCTG CGTGGGCTCT GTCCTCAGGG TGGCCCGCCG TAGTCCCCCT    480

CCCCACTCTG AGTTTCCTGT CCCAAAGTCC TAAGGAAGTT TCCAGAACTA CATCTCACCA    540

TCTTGAGTCA GCCTTGGCTC AGTGTCCATC TCACAGGCCT GGAAGGGGCA GGAGTCAGCA    600

CTGTCCAGAC CACAGGGCCT GAGTGTGGGG AGGGCAGCCG TCTAGGAAGG TGGTGGAGG     660

TTGTTACCTT GAGGCAAGAG GGCTGCGGGG CAGAAAGACA CAGCAGGTGA CTGTTGTGGG    720

AGGCCCAAGA GAGGCCTGGG AGAGGGATGG CCCACAAGGG CTGACCCTCC CGCCACCCAG    780

GGGGCCTTGG ACAGGTTTCC TCCTGGCAGG GTGGCCCTTG TGCATGGAAC CCCTACAACG    840

ACTAAGGCTG GCAGGCATGA GGTTTCCTGA AGGAGAAAGA GCTTGTGGGG CCCAGTGTGG    900

CTGGGGGGGC GCTGGGACTC CATTCTGAAG CCAAAGGCAC TGGGAAGGGC TTCCGCAGAG    960

GAGGGTTTGG CAGGGGTTGC CAGGAACAGC CTGGATGGGG ACAGGGAACA GATAAGGTGG   1020

GTGGAGGAGT TAGCCGGGAG CCTGGGGCTG GCTCCAGCAT GATGTGGGGG TCTGCAAGGC   1080

CCTGGAGAAA GTGGGGTGGT GCAGCAGGGG GCACACCCAC AGCTGGAGCT GACCCAGATG   1140

GACAGCTTGG GCTCTGCCAC GCGGGACTAG GCAAGGAAGG GGCACGAACA AGCAGGAAGT   1200

GGTGAGGCGG TCTCCAGCTA GCTGCTCTCC CCTGCCCAGA CTTTGGTTTC CTCCCTGCTG   1260

GCTTGGCCTG GCTCCCTGGC TCTGTGTGGT ATGGTCACAC CCCCGTGCAC CCCCTCCACT   1320

GAGATGGGGC GGGGAGAGCA CCGAGGCTGC TCTTCCTCTC CTGGGCCGTC CTCTGAGCAG   1380

CAGACGGGGC TAAGCGTTCC CCAGCTCGCC TTCACACACA GCCCGTGCCA CCACACCGAC   1440

GGTACCATGA AGGACGAGGT AGCTCTACTG GCTGCTGTCA CCCTCCTGGG AGTCCTGCTG   1500

CAAGGTGGGC TGGTTCCTAT CTAGGAAGAG GGTGGGCCTT AGATCCCTAC AGCTTGCCCT   1560

CTGCCCCCTA GGCCCAGGTG GAGGGCAGAG GTGGGACTC  CAGCCCAGGC CCAAGCTGGA   1620

AGAGGGTGGG GACTTTCAGG GAACTGGGGG GCACCTGGCT GTGAGAGCTG TAGGACTTGG   1680

GGGTGGCAAG GGTGCCAGGA CAAATGGTAG GATAGCCATG GGCTTGGGGA AGCTGATCTC   1740

TGCTCTTTCC AGCTGTCCCC TCTCTGGGCG TCCCAGCAAG CGGCCCCCAT TCCCTGGCTC   1800

TGCTTCAAAG GCACCTCCAT ACTGGGACCA CGTGGAGCAG GGTAGAGGTG GGACTCCTTC   1860

CTCCAGCCCC CTAAAAAGAG CCTGCTTAAT GCCTTTCTCA GACTGGCCCT AAAGGACACA   1920

TTCCTTGGCC AGATATCCTT GCCACCTAAG AGACACCACT ACTCCACAGT GTGTGGGCTA   1980

GGATAAGGCA CAGCCTGGGG AGGGGCTCT  GAAGGGGCTG AACAGACAGG CCAGCCTGAC   2040

CTCCAGCTGC TCCTGCACTG AGCTGGATGG CCACCCTGTG ACACCCATCT GCAGAGGGCC   2100

CAGAACCAAA GGTGCCAGGG CTGCAGGACT CAGGGGGAGA TGGTCCGACG GGAGGTCTGG   2160

GGAGGGAGCG CACAGCCAGC ACTGGTCTGT GTGTGGTCTG GCCTGGCCTC ACCTGACCAA   2220

GAGAAGGGCT CCTGCCCACA GAGAAACTTT AGGGCCAGCC CACCCTCTGC AACTACCCCA   2280

GCCCTGGGGT CCTGGGGTTA GGCTAGGAGA GTCCCAGCTG CAACCTCCTG GGAGCAGGAG   2340

AGAAGGTGTC TGTCAGATTT AGGCCTGGGA CCGGAATGCA GGAACAGAGA AACTGAGGTT   2400

TGGAGGCACA GGGACGCAGG CTTTAGTGAT CCCGGCCTGA GGCAGGGTCA GAGGGCCCTG   2460

CTGGTGGGCG CTGGTAGGTG GGTGACCAGG GACTGTTAGC TACAGGGAGT GTGCTTCCTT   2520

GCACCTGGGA GGATGCAGCC AGCTCTGCCC TCAGACTCCC GAGGCACTTC CTGGCCAGGG   2580

ACCTGAAAGC TGCATTTGCC TGTGTTTTGA GAGTGAAATG ATTCAGAAAC AAGGACTCAA   2640
```

```
GTGGTCTCTC TCGCGGAGCA GGTGTCCCTG TGCCTGAATC ACTCACCCTC CCCCATACAC    2700

TCACAGGTTG GGACAGGGCC TCTCTGCGCC CCAGGCTTCA GCCCTGCCCT CCTCGCTGAA    2760

TGTCAGGGAC ACAGGGCAGG CCAGGGATGG GTGAGACGAG AGGTCTCCTC GGGCGGGGAG    2820

GGGGCGGGGT TCCGCCTTAG GGAGGAGAGG ACACGGCCAA GTGAAGGGCC AGATTGCAGG    2880

ATCCCTCCCA CTCCCATCTC TGGGGCTTCG GGTGTCCAGA CCTGACTCCC GCTCCCCCTC    2940

CTCCCCCAGC CTACTTCTCC CTGCAGGTGA TCTCGGCGCG CAGGGCCTTC CGCGTGTCGC    3000

CGCCGCTCAC CACCGGCCCA CCCGAGTTCG AGCGCGTCTA CCGAGCCCAG TGAGGCGCGG    3060

CGGGAGGGCG CGGGGCGGGG AGCGAGCCCC AGGCGGGTCC GGGTCGCAGG ACCATCCCGG    3120

CCGGCGCGCT CATCCCACCC GCCCACCGCA GGGTGAACTG CAGCGAGTAC TTCCCGCTGT    3180

TCCTCGCCAC GCTCTGGGTC GCCGGCATCT TCTTTCATGA AGGTCGGGGT GTGGGCAGG    3240

GGCGCACGCG CTGGACCCCC GGGACCCGCG CAGGGCGCTC ACCAGGCCCG TGCGTACCTC    3300

TCGCAGGGGC GGCGGCCCTG TGCGGCCTGG TCTACCTGTT CGCGCGCCTC CGCTACTTCC    3360

AGGGCTACGC GCGCTCCGCG CAGCTCAGGT GAGGGCCGGG CGGGGAGCGG GGCGGGGCCG    3420

GGGAAAGATC GCGGGCGGGC GGGGCTCCTG GGGAGCGGGA CCGAAGCTGG GGGCGGGCGA    3480

CGGGCCGGAG CCCAGCGCCT TTGGGGATTC GGTGGGCGAG CCCTGGCGGC GGCCAGAGGA    3540

AGTCCCCGTG GGGCCAGGGT TGCGGCGGGG AAGAAGCGGG CCTCCTCGCG CCACCTCCCC    3600

GCTGACCGCC GCCCGCAGGC TGGCACCGCT GTACGCGAGC GCGCGCGCCC TCTGGCTGCT    3660

GGTGGCGCTG GCTGCGCTCG GCCTGCTCGC CCACTTCCTC CCGGCCGCGC TGCGCGCCGC    3720

GCTCCTCGGA CGGCTCCGGA CGCTGCTGCC GTGGGCCTGA GACCAAGGCC CCCGGGCCGA    3780

CGGAGCCGGG AAAGAAGAGC CGGAGCCTCC AGCTGCCCCG GGGAGGGGCG CTCGCTTCCG    3840

CATCCTAGTC TCTATCATTA AAGTTCTAGT GACCGAGACC CGGGCTGCGT TCTCTGGGTC    3900

CGCGGGGGTG GCGCACCGCG GGCTACGGAG CCTGGAGGGG CCCAGCCCGA GTCCGGGCAG    3960

CCCGGGGCGG GCTTCCTAGT GGCGGCGTGA GAGTGGCTGC GAAGGAACGA GCCCTCCCCC    4020

TGGGCGGGA CTGGATCCGG TCTTCACCTC CTACCCCACT CCCTACTCAG CCTCGGGGTC    4080

ACAAGGCCGC CCAGTCCTGC CGGGGTTCAC CCTCCTAGCG CTCAGCGGTC TCCTCACCGG    4140

TCCCCCTCCT CAGGGGCCTT CCCTCGACTC TCAGCCGCCG CAGTCCCTCG TCCCCTGGCC    4200

TTCACAGCTG ACACTAGATA GAGCCTGTGG CTCTCTCCCC AGGTGAGGGC AGGGGTTTTT    4260

CTTTTGGTCA GCACTGGATC CCCCTCGTTA ACTGTAGGTG TTCAGGGCAG CCCTCCGAGG    4320

TCCGCAGAGC TGCGGGCACC ATGGGAACGA AGTGAGTCAG TGACAGGCGG TCTCAAGGAA    4380

ATGTCCAGAA GCCTTGGGGA TCCAGGGGAG GCCCACAGAA ACAAAGAAGT GACTTTTAGC    4440

CAAGTATGCA GGAGAAACGG AGGAG                                        4465
```

(2) INFORMATION FOR SEQ ID NO: 2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 2:

```
GGGGCGGCCG GGGGCGCTCC AGGCGGGGCA                                      30
```

```
(2) INFORMATION FOR SEQ ID NO: 3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 3:

CTTGGACAGG TTTCCTCCTG GCAGGGTGGA                                      30

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 4:

GGGTTGCCAG GAACAGCCTG GATGGGGACC                                      30

(2) INFORMATION FOR SEQ ID NO: 5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 5:

ATGGTCCGAC GGGAGGTCTG GGGAGGGAGT                                      30

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 6:

CTCCTGCCTG GAGTTCTGGG TGTCTCCCTT                                      30

(2) INFORMATION FOR SEQ ID NO: 7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 7:

TAGTCGTTGT AGGGGTTCCA TGCACAAGGT                                      30

(2) INFORMATION FOR SEQ ID NO: 8:

(i) SEQUENCE CHARACTERISTICS:
        (A) LENGTH: 30 base pairs
```

(B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 8:

TAACTCCTCC ACCCACCTTA TCTGTTCCCG                    30

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 9:

GACCACACAC AGACCAGTGC TGGCTGTGCA                    30

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 10:

GGAGTTCTGG GTGTCTCCAT C                             21

(2) INFORMATION FOR SEQ ID NO: 11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 11:

GGAGTTCTGG GTGTCTCCAT T                             21

(2) INFORMATION FOR SEQ ID NO: 12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 12:

TAGGGGTTCC ATGCACAAGG G                             21

(2) INFORMATION FOR SEQ ID NO: 13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 13:

TAGGGGTTCC ATGCACAATG G                                    21

(2) INFORMATION FOR SEQ ID NO: 14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 14:

TAGGGGTTCC ATGCACAAGG T                                    21

(2) INFORMATION FOR SEQ ID NO: 15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 15:

TAGGGGTTCC ATGCACAATG T                                    21

(2) INFORMATION FOR SEQ ID NO: 16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 16:

CACCCACCTT ATCTGTTCCC T                                    21

(2) INFORMATION FOR SEQ ID NO: 17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 17:

CACCCACCTT ATCTGTTCCC G                                    21

(2) INFORMATION FOR SEQ ID NO: 18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 18:

GGAACAGCCT GGATGGGGTC A                                              21

(2) INFORMATION FOR SEQ ID NO: 19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 19:

GGAACAGCCT GGATGGGGTC C                                              21

(2) INFORMATION FOR SEQ ID NO: 20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 20:

CAGACCAGTG CTGGCTGTAC G                                              21

(2) INFORMATION FOR SEQ ID NO: 21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 21:

CAGACCAGTG CTGGCTGTAC A                                              21

(2) INFORMATION FOR SEQ ID NO: 22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 22:

GGTCAGTCTG GACTTTGCCA C                                              21

(2) INFORMATION FOR SEQ ID NO: 23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 23:

TTGTTACCTT GAGGCAAGAG G                                              21

(2) INFORMATION FOR SEQ ID NO: 24:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 24:

AGGCTGGCAG GCATGAGGTT T                                                   21

(2) INFORMATION FOR SEQ ID NO: 25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 25:

TTCGTGCCCC TTCCTTGCCT A                                                   21

(2) INFORMATION FOR SEQ ID NO: 26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 26:

CTCCAGCTGC TCCTGCACTG A                                                   21
```

METHODS FOR ANALYZING LTC4 SYNTHASE POLYMORPHISMS AND DIAGNOSTIC USE

This application is the national phase of international application PCT/GB98/02468 filed Aug. 18, 1998 which designated the U.S.

This invention relates to polymorphisms in the $LTC_4$ synthase gene. The invention also relates to methods and materials for analysing allelic variation in the $LTC_4$ synthase gene, and to the use of $LTC_4$ synthase polymorphism in the diagnosis and treatment of leukotriene mediated diseases such as asthma and allergic rhinitis.

The cysteinyl-leukotrienes, $LTC_4$, $LTD_4$ and $LTE_4$, are potent bronchoconstrictors, increase vascular permeability and increase mucus production in airways. They are implicated in the pathophysiology of asthma and allergic rhinitis and are found at elevated levels in bronchoalveolar lavage from asthma patients, particularly after allergen challenge $LTD_4$ and $LTE_4$ may also enhance the neurogenic inflammatory response in airways. Compounds which inhibit leukotriene synthesis e.g. the 5-lipoxygenase inhibitor, zileuton, or the leukotriene receptor antagonist, zafirlukast, have been shown to be effective against asthma and rhinitis (Busse W. W, Clin. Exp. Allergy, 26, 868–879, 1996; see particularly FIG. 1 therein which shows the arachidonic acid cascade, indicating the role of $LTC_4$ synthase in catalysing the formation of $LTC_4$).

Leukotrienes are derived from membrane phospholipids. Arachidonic acid is released from the phospholipid by cytosolic phospholipase A2 and converted to $LTA_4$ by 5-lipoxygenase in the presence of 5-lipoxygenase activating protein, FLAP. Polymorphisms in 5-LO have been reported in international patent application WO 97/42347, Brigham & Women's Hospital. $LTA_4$ is conjugated with reduced glutathione by $LTC_4$ synthase to form $LTC_4$. The biologically active metabolites, $LTD_4$ and $LTE_4$ are formed, following carrier mediated export of $LTC_4$, by the sequential action of gamma-glutamyl transpeptidase and dipeptidases.

The $LTC_4$ synthase gene has been cloned and published as a 4,465 nucleotide genomic sequence comprising 1,446 nucleotides of sequence 5' to the coding sequence, the 5 exons and intervening introns and 3' sequence extending 398 nucleotide beyond the poly A signal (Penrose et al., J. Biol. Chem., 271, 11356–11361, 1996; EMBL accession no. U50136).

One approach is to use knowledge of polymorphisms to help identify patients most suited to therapy with particular pharmaceutical agents (this is often termed "pharmacogenetics"). Pharmacogenetics can also be used in pharmaceutical research to assist the drug selection process. Polymorphisms are used in mapping the human genome and to elucidate the genetic component of diseases. The reader is directed to the following references for background details on pharmacogenetics and other uses of polymorphism detection: Linder et al. (1997), Clinical Chemistry, 43, 254; Marshall (1997), Nature Biotechnology, 15, 1249; International Patent Application WO 97/40462, Spectra Biomedical; and Schafer et al. (1998), Nature Biotechnology, 16, 33.

Clinical trials have shown that patient response to treatment with leukotriene antagonists is heterogeneous. Thus there is a need for improved approaches to pharmaceutical agent design and therapy with leukotriene antagonists.

The present invention is based on the discovery of five single nucleotide polymorphisms (SNPs) in the $LTC_4$ synthase gene. Three SNPs have been found in the 5' untranslated region of the gene and two in the first intron, located at positions 375, 815, 1003, 2169 and 2742 respectively, based on the numbering of U50136. Before our first filing date, we believe there has been no disclosure of polymorphism/allelic variation in the $LTC_4$ synthase gene.

According to one aspect of the present invention there is provided a method for the diagnosis of a single nucleotide polymorphism in $LTC_4$ synthase in a human, which method comprises determining the sequence of the nucleic acid of the human at one or more of positions 375, 815, 1003, 2169 and 2742 in the $LTC_4$ synthase gene as defined by the positions in SEQ ID NO: 1, and determining the status of the human by reference to polymorphism in the $LTC_4$ synthase gene.

The term human includes both a human having or suspected of having a leukotriene mediated disease and an a symptomatic human who may be tested for predisposition or susceptibility to leukotriene mediated disease. At each position the human may be homozygous for an allele or the human may be a heterozygote.

In one embodiment of the invention preferably the method for diagnosis described herein is one in which the single nucleotide polymorphism at position 375 is presence of G and/or A.

In another embodiment of the invention preferably the method for diagnosis described herein is one in which the single nucleotide polymorphism at position 815 is presence of C and/or A.

In another embodiment of the invention preferably the method for diagnosis described herein is one in which the single nucleotide polymorphism at position 1003 is presence of A and/or C. Testing for the presence of the C allele at this position is especially preferred because, without wishing to be bound by theoretical considerations, of its association with increased levels of $LTC_4$ synthase (as explained herein).

In another embodiment of the invention preferably the method for diagnosis described herein is one in which the single nucleotide polymorphism at position 2169 is presence of C and/or T.

In another embodiment of the invention preferably the method for diagnosis described herein is one in which the single nucleotide polymorphism at position 2742 is presence of C and/or T.

The method for diagnosis is preferably one in which the sequence is determined by a method selected from amplification refractory mutation system and restriction fragment length polymorphism.

In another aspect of the invention we provide a method for the diagnosis of leukotriene mediated disease, which method comprises:
i) obtaining sample nucleic acid from an individual,
ii) detecting the presence or absence of a variant nucleotide at one or more of positions 375, 815, 1003 and 2169 in the $LTC_4$ synthase gene and
iii) determining the status of the individual by reference to polymorphism in the $LTC_4$ synthase gene.

The published sequence of the $LTC_4$ synthase gene, EMBL accession number U50136, is shown in SEQ ID NO: 1 in which the variant sites discovered in the present invention are at positions 375, 815, 1003, 2169 and 2742.

Allelic variation at position 375 consists of a single base substitution from G (the published base), for example to A. Allelic variation at position 815 consists of a single base substitution from C (the published base), for example to A. Allelic variation at position 1003 consists of a single base substitution from A (the published base), for example to C. Allelic variation at position 2169 consists of a single base substitution from C (the published base), for example to T. Allelic variation at position 2742 consists of a single base substitution from C (the published base), for example to T. The status of the individual may be determined by reference to allelic variation at one, two, three, four or all five of the above loci.

Sanak et al. (1998), Lancet, 350, 1599, have reported an increased risk of aspirin induced asthma (AIA) being associated with the polymorphism at position 1003. This work suggests that the presence of the C allele at position 1003 leads to increased levels of $LTC_4$ synthase (see also Cowburnet al. (1998), J. Clin. Invest., 101, 834). AIA affects about 10% of adult asthmatics. Aspirin and other cyclooxygenase inhibitors cause release of LTs into airways, leading to an asthma attack in susceptible individuals. Clinical approaches to deal with AIA include pretreatment with anti-leukotriene drugs (Szczeklik (1997), Allergy, 52, 613–9). Commentators have written approvingly of the clinical utility of detection of $LTC_4$ polymorphisms (Holgate (1998), Lancet, 351, 1300–1301, see last paragraph in particular). Anti-leukotriene drugs have been reviewed in the following publications: Horwitz et al. (1998), Am J Respir Crit Care Med, 157, 1363 (see particularly Table 1 for a list of drugs); and Tan (1998), Current Opinion in Pulmonary Medicine, 4, 25.

The test sample of nucleic acid is conveniently a sample of blood, bronchoalveolar lavage fluid, sputum, or other body fluid or tissue obtained from an individual. It will be appreciated that the test sample may equally be a nucleic acid sequence corresponding to the sequence in the test sample, that is to say that all or a part of the region in the sample nucleic acid may firstly be amplified using any convenient technique e.g. PCR, before use in the analysis of $LTC_4$ synthase variation.

It will be apparent to the person skilled in the art that there are a large number of analytical procedures which may be used to detect the presence or absence of variant nucleotides at one or more of positions 375, 815, 1003, 2169 and 2742 in the $LTC_4$ synthase gene. In general, the detection of allelic variation requires a mutation discrimination technique, optionally an amplification reaction and a signal generation system. Table 1 lists a number of mutation detection techniques, some based on the PCR. These may be used in combination with a number of signal generation systems, a selection of which is listed in Table 2. Further amplification techniques are listed in Table 3. Many current methods for the detection of allelic variation are reviewed by Nollau et al., Clin. Chem. 43, 1114–1120, 1997; and in standard textbooks, for example "Laboratory Protocols for Mutation Detection", Ed. by U. Landegren, Oxford University Press, 1996 and "PCR", $2^{nd}$ Edition by Newton & Graham, BIOS Scientific Publishers Limited, 1997.

| Abbreviations: | |
|---|---|
| AIA | Aspirin induced asthma |
| ALEX ™ | Amplification refractory mutation system linear extension |
| APEX | Arrayed primer extension |
| ARMS ™ | Amplification refractory mutation system |
| b-DNA | Branched DNA |
| CMC | Chemical mismatch cleavage |
| bp | base pair |
| COPS | Competitive oligonucleotide priming system |
| DGGE | Denaturing gradient gel electrophoresis |
| FLAP | 5-lipoxygenase activating protein |
| FRET | Fluorescence resonance energy transfer |
| LCR | Ligase chain reaction |

| -continued | |
|---|---|
| Abbreviations: | |
| 5-LO | 5-Lipoxygenase |
| LT | Leukotriene |
| MASDA | Multiple allele specific diagnostic assay |
| NASBA | Nucleic acid sequence based amplification |
| OLA | Oligonucleotide ligation assay |
| PCR | Polymerase chain reaction |
| PTT | Protein truncation test |
| RFLP | Restriction fragment length polymorphism |
| SDA | Strand displacement amplification |
| SNP | Single nucleotide polymorphism |
| SSCP | Single-strand conformation polymorphism analysis |
| SSR | Self sustained replication |
| TGGE | Temperature gradient gel electrophoresis |

Table 1—Mutation Detection Techniques
General: DNA sequencing, Sequencing by hybridisation
Scanning: PJT*, SSCP, DOGE, TGGE, Cleavase, Heteroduplex analysis, CMC, Enzymatic mismatch cleavage
* Note: not useful for detection of promoter polymorphisms.
Hybridisation Based
  Solid phase bybridisation: Dot blots, MASDA, Reverse dot blots, Oligonucleotide arrays (DNA Chips)
  Solution phase hybridisation: Taqman™—U.S. Pat. No. 5,210,015 & 5,487,972 (Hoffmann-La Roche), Molecular Beacons—Tyagi et al (1996), Nature Biotechnology, 14, 303; WO 95/13399 (Public Health Inst., New York)
Extension Based: ARMS™, ALEX™—European Patent No. EP 332435 B1 (Zeneca Limited), COPS—Gibbs et al (1989), Nucleic Acids Research, 17, 2347.
Incorporation Based: Mini-sequencing, APEX
Restriction Enzyme Based: RFLP, Restriction site generating PCR
Ligation Based: OLA
Other: Invader assay
Table 2—Signal Generation or Detection Systems
Fluorescence: FRET, Fluorescence quenching, Fluorescence polarisation—United Kingdom Patent No. 2228998 (Zeneca Limited)
Other: Cherniluminescence, Electrochemiluminescence, Raman, Radioactivity, Colorimetric, Hybridisation protection assay, Mass spectrometry
Table 3—Further Amplification Methods
SSR, NASBA, LCR, SDA, b-DNA Preferred mutation detection techniques include ARMS™, ALEX™, COPS, Taqman, Molecular Beacons, RFLP, and restriction site based PCR and FRET techniques.

Particularly preferred methods include ARMS™ and RFLP based methods. ARM™ is an especially preferred method.

In a further aspect, the diagnostic methods of the invention are used to assess the efficacy of therapeutic compounds in the treatment of asthma, rhinitis and other leukotriene mediated diseases. The polymorphisms identified in the present invention occur in the 5' untranslated region and the first intron of the $LTC_4$ synthase gene, regions which are of importance in the control of gene transcription and gene translation. Furthermore, each of the variant positions is located within a known transcription factor binding site; it is believed that substitution of A at variant position 375 modifies an AP-2 CS4 transcription factor binding site, substitution of A at variant position 815 modifies an AP-2 CS5 transcription factor binding site, substitution of C at variant position 1003 modifies the glucocorticoid receptor binding site GGGACA and substitution of T at variant position 2169 disrupts an MREc-(3) transcription factor binding site.

Example 3 below describes another polymorphism which is substitution of T for C at position 2742. This variant disrupts a RIPE3b site (Shieh and Tsai, J. Biol. Chem. 266, 16708–16714, 1991).

Assays, for example reporter-based assays, may be devised to detect whether one or more of the above polymorphisms affect transcription levels and/or message stability.

Individuals who carry particular allelic variants of the $LTC_4$ synthase gene may therefore exhibit differences in their ability to regulate enzyme biosynthesis under different physiological conditions and will display altered abilities to react to different diseases. In addition, differences in enzyme regulation arising as a result of allelic variation may have a direct effect on the response of an individual to drug therapy. $LTC_4$ synthase polymorphism may therefore have the greatest effect on the efficacy of drugs designed to modulate the activity of $LTC_4$ synthase or other components of the leukotriene pathway. However, the polymorphisms may also affect the response to agents acting on other biochemical pathways regulated by leukotrienes. The diagnostic methods of the invention may therefore be useful both to predict the clinical response to such agents and to determine therapeutic dose.

In a further aspect, the diagnostic methods of the invention, are used to assess the predisposition and/or susceptibility of an individual to diseases mediated by leukotrienes. $LTC_4$ synthase polymorphism may be particularly relevant in the development of asthma and other inflammatory diseases such as allergic rhinitis and the present invention may be used to recognize individuals who are particularly at risk from developing these conditions.

In a further aspect, the diagnostic methods of the invention are used in the development of new drug therapies which selectively target one or more allelic variants of the $LTC_4$ synthase gene. Identification of a link between a particular allelic variant and predisposition to disease development or response to drug therapy may have a significant impact on the design of new drugs. Drugs may be designed to regulate the biological activity of variants implicated in the disease process whilst minimizing effects on other variants.

In a further diagnostic aspect of the invention the presence or absence of variant nucleotides is detected by reference to the loss or gain of sites recognized by restriction enzymes. In the accompanying Example 1 we provide details of convenient sites that are lost or gained as a result of $LTC_4$ synthase gene polymorphisms. The person of ordinary skill will be able to design and implement diagnostic procedures based on the detection of restriction fragment length polymorphism due to the loss or gain of one or more of the sites listed in Examples 1 or 3.

In yet a further aspect the invention provides a variant of the $LTC_4$ synthase gene comprising one or more of the specific polymorphisms at positions 375, 815, 1003 and 2169.

Further aspects of this invention comprise the 5' untranslated region of the $LTC_4$ synthase gene comprising a polymorphism at one or more of positions 375, 815 and 1003. In particular the polymorphism at position 375 is G to A. In particular the polymorphism at position 815 is C to A. In particular the polymorphism at position 1003 is A to C. Another aspect of this invention comprises the first intron of the $LTC_4$ synthase gene comprising a polymorphism at position 2169; in particular this polymorphism is C to T.

According to another aspect of the present invention there is provided a nucleic acid comprising the 5' untranslated region of $LTC_4$ synthase comprising a polymorphism corresponding with one or more of positions 375, 815 and 1003 as defined by the positions in SEQ ID NO: 1 and in which there is an A at position 375, an A at position 815 and a C at position 1003. The 5' untranslated region of $LTC_4$ synthase is defined as positions 1–1446 of SEQ ID NO: 1. Fragments of the 5' untranslated region comprising at least one of these allelic variants are also within the scope of the invention.

Fragments are at least 17 bases, more preferably at least 20 bases, more preferably at least 30 bases. Complementary strands are also within the scope of the invention.

According to another aspect of the present invention there is provided a nucleic acid comprising the first intron of the $LTC_4$ synthase gene comprising a polymorphism at one or more of positions 2169 and 2742 as defined by the position in SEQ ID NO: 1 and in which there is a T at position 2169 and there is a T at position 2742. The first intron of the $LTC_4$ synthase gene is defined as positions 1505–2949 of SEQ ID NO: 1. Fragments of the first intron comprising at least one of these allelic variants are also within the scope of the invention.

The invention further provides nucleotide primers which detect the $LTC_4$ synthase gene polymorphisms of the invention.

According to another aspect of the present invention there is provided a diagnostic nucleic acid primer capable of detecting a $LTC_4$ synthase gene polymorphism at one or more of positions 375, 815, 1003, 2169 and 2742 in the $LTC_4$ synthase gene as defined by the in SEQ ID NO: 1.

A diagnostic nucleic acid primer is defined as an allele specific primer, used, generally together with a constant primer, in an amplification reaction such as a PCR reaction, which provides the discrimination between alleles through selective amplification of one allele at a particular sequence position e.g. as used for ARMS™ assays, see Example 2 herein. The diagnostic primer is preferably 17–50 nucleotides, more preferably about 17–35 nucleotides, more preferably about 17–30 nucleotides.

We provide diagnostic primers comprising the sequences set out below as well as derivatives thereof wherein about 6–8 of the nucleotides at the 3' terminus are identical to the sequences given below and wherein up to 10, such as up to 8, 6, 4, 2, or 1 of the remaining nucleotides may be varied without significantly affecting the properties of the diagnostic primer. Conveniently, the sequence of the diagnostic primer is as written below, or more preferably as described in Example 2 below. The diagnostic primer is preferably 17–50 nucleotides, more preferably about 17–35 nucleotides, more preferably about 17–30 nucleotides.

| Primer number* | Allelic variant detected | Diagnostic (Allele Specific) Primer sequence |
| --- | --- | --- |
| 1 | 375 A | GGGGCGGCCGGGGGCGCTCCAGGCGGGGCA |
| 2 | 815 A | CTTGGACAGGTTTCCTCCTGGCAGGGTGGA |
| 3 | 1003 C | GGGTTGCCAGGAACAGCCTGGATGGGGACC |
| 4 | 2169 T | ATGGTCCGACGGGAGGTCTGGGGAGGGAGT |
| 5 | 375 A | CTCCTGCCTGGAGTTCTGGGTGTCTCCCTT |
| 6 | 815 A | TAGTCGTTGTAGGGGTTCCATGCACAAGGT |

-continued

| Primer number* | Allelic variant detected | Diagnostic (Allele Specific) Primer sequence |
|---|---|---|
| 7 | 1003 C | TAACTCCTCCACCCACCTTATCTGTTCCCG |
| 8 | 2169 T | GACCACACACAGACCAGTGCTGGCTGTGCA |

*Primers 1–8 are represented as SEQ ID NO: 2–9 respectively.

The primers may be manufactured using any convenient method of synthesis. Examples of such methods may be found in standard textbooks, for example "Protocols for Oligonucleotides and Analogues; Synthesis and Properties," Methods in Molecular Biology Series; Volume 20; Ed. Sudhir Agrawal, Humana ISBN: 0-89603-247-7; 1993; $1^{st}$ Edition. If required the primer(s) may be labelled to facilitate detection.

According to another aspect of the present invention there is provided an allele-specific oligonucleotide probe capable of detecting a $LTC_4$ synthase gene polymorphism at one or more of positions 375, 815, 1003, 2169 and 2742 in the $LTC_4$ synthase gene as defined by the positions in SEQ ID NO: 1.

The allele-specific oligonucleotide probe is preferably 17–50 nucleotides, more preferably about 17–35 nucleotides, more preferably about 17–30 nucleotides.

The design of such probes will be apparent to the molecular biologist of ordinary skill. Such probes are of any convenient length such as up to 50 bases, up to 40 bases, more conveniently up to 30 bases in length, such as for example 8–25 or 8–15 bases in length. In general such probes will comprise base sequences entirely complementary to the corresponding wild type or variant locus in the $LTC_4$ gene. However, if required one or more mismatches may be introduced, provided that the discriminatory power of the oligonucleotide probe is not unduly affected. The probes of the invention may carry one or more labels to facilitate detection.

According to another aspect of the present invention there is provided a diagnostic kit comprising a diagnostic primer of the invention and/or an allele-specific oligonucloetide primer of the invention.

The diagnostic kits may comprise appropriate packaging and instructions for use in the methods of the invention. Such kits may further comprise appropriate buffer(s) and polymerase(s) such as thermostable polymerases, for example taq polymerase.

The $LTC_4$ synthase gene has been mapped to chromosome 5q35 (Penrose et al, J. Biol. Chem. 271, 11356–11361, 1996). In another aspect of the invention, the single nucleotide polymorphisms of this invention may be used as genetic markers for this region in linkage studies. This particularly applies to the polymorphism at 1003 because of its relatively high frequency, (Krugylak, Nature Genetics, 17, 21–24, 1997).

According to another aspect of the present invention there is provided a method of treating a human in need of treatment with an antileukotriene drug in which the method comprises:

i) diagnosis of a single nucleotide polymorphism in $LTC_4$ synthase in the human, which diagnosis comprises determining the sequence of the nucleic acid at one or more of positions 375, 815, 1003, 2169 and 2742 in the $LTC_4$ synthase gene as defined by the positions in SEQ ID NO: 1, and determining the status of the human by reference to polymorphism in the $LTC_4$ synthase gene; and ii) administering an effective amount of an antileukotriene drug.

Preferably determination of the status of the human is clinically useful. Examples of clinical usefulness include deciding which antileukotriene drug or drugs to administer and/or in deciding on the effective amount of the drug or drugs.

According to another aspect of the present invention there is provided use of an antileukotriene drug in preparation of a medicament for treating a leukotriene mediated disease in a human diagnosed as having a single nucleotide polymorphism at one or more of positions 375, 815, 1003, 2169 and 2742 in $LTC_4$ synthase gene as defined by the positions in SEQ ID NO: 1.

According to another aspect of the present invention there is provided a pharmaceutical pack comprising an antileukotriene drug and instructions for administration of the drug to humans diagnostically tested for a single nucleotide polymorphism at one or more of positions 375, 815, 1003, 2169 and 2742 in $LTC_4$ synthase gene as defined by the positions in SEQ ID NO: 1.

Suitable antileukotriene drugs include leukotriene $D_4$ receptor antagonists, FLAP antagonists and 5-lipoxygenase inhibitors (see particularly Table 1 in the following publication for a list of drugs, Horwitz et al. (1998), Am J Respir Crit Care Med, 157, 1363), preferably leukotriene $D_4$ receptor antagonists, more preferably montelukast and zafirlukast, and of these zafirlukast is most preferred.

Testing for the presence of the C allele at position 1003 is especially preferred because, without wishing to be bound by theoretical considerations, of its association with increased levels of $LTC_4$ synthase (as explained herein).

The invention will now be illustrated but not limited by reference to the following Examples. All temperatures are in degrees Celsius.

In the Examples below, unless otherwise stated, the following methodology and materials have been applied.

AMPLITAQ™, available from Perkin-Elmer Cetus, is used as the source of thermostable DNA polymerase.

General molecular biology procedures can be followed from any of the methods described in "Molecular Cloning—A Laboratory Manual" Second Edition, Sambrook, Fritsch and Maniatis (Cold Spring Harbor Laboratory, 1989).

Electropherograms were obtained in a standard manner: data was collected by ABI377 data collection software and the wave form generated by ABI Prism sequencing analysis (2.1.2).

EXAMPLE 1

Identification of Polymorphisms

1. Methods

DNA Preparation

DNA was prepared from frozen blood samples collected in EDTA following protocol 1 (Molecular Cloning: A Laboratory Manual, p392, Sambrook, Fritsch and Maniatis, $2^{nd}$ Edition, Cold Spring Harbor Press, 1989) with the following modifications. The thawed blood was diluted in an equal volume of standard saline citrate instead of phosphate buffered saline to remove lysed red blood cells. Samples were extracted with phenol, then phenol/chloroform and then chloroform rather than with three phenol extractions. The DNA was dissolved in deionised water.

Template Preparation

Templates were prepared by PCR using the oligonucleotide primers and annealing temperatures set out below. The extension temperature was 72° and denaturation temperature 94°. Generally 50 ng of genomic DNA was used in each reaction and subjected to 40 cycles of PCR.

| Fragment | Forward Oligonucleotide | Reverse Oligonucleotide | Annealing Temperature | Time | % DMSO |
|---|---|---|---|---|---|
| 62–1043 | 62–87 | 1021–1043 | 62° | 60 s | 5 |
| 271–407 | 271–291 | 388–407 | 60° | 45 s | 0 |
| 417–1043 | 417–437 | 1021–1043 | 60° | 45 s | 10 |
| 851–1824 | 851–874 | 1801–1824 | 62° | 60 s | 5 |
| 1503–2400 | 1503–1524 | 2379–2400 | 65° | 60 s | 10 |

For dye-primer sequencing these primers were modified to include T7 and SP6 primer sequences (ABI protocol P/N 402114, Applied Biosystems) at the 5' end of the forward and reverse oligonucleotides respectively.

Chemical Mismatch Cleavage (CMC)

CMC was carried out as described by Rowley el al. (Genomics 30, 574–582, 1995) using internal labelling of probe and target with fluorescent dyes (RG6 or R110). 6% Acrylamide gels were run on an automated DNA sequencer (ABI 377, Applied Biosystems) on 12 cm plates (under module GS12-2400A) and analysed with suitable software (ABI GeneScan™ 2.1).

Dye Primer Sequencing

Dye-primer sequencing using T7 and SP6 primers was as described in the ABI protocol P/N 402114 for the ABI Prism™ dye primer cycle sequencing core kit with "Ampli-Taq FS"™ DNA polymerase, modified in that the annealing temperature was 45° and DMSO was added to the cycle sequencing mix to a final concentration of 5%.

The extension reactions for each base were pooled, ethanol/sodium acetate precipitated, washed and resuspended in formamide loading buffer.

4.25% Acrylamide gels were run on an automated sequencer (ABI 377, Applied Biosystems).

2. Results

All positions are based on the U50136 numbering.

Variant Position 375

CMC analysis of fragment 1 (62–1043) produced cleavage products of approximately 300 bp and 670 bp in 9/49 subjects. Dye-primer sequence analysis of fragment 1 from 2 subjects showing this pattern revealed a substitution of A for G at position 375. This was confirmed by sequencing 6 clones of fragment 1 from one of these subjects; 5/6 had A at position 375 and 1/6 had G.

Substituting A for G at position 375 modifies a Mnl I site at position 368. PCR products from $LTC_4$ synthase position 271 to 407 from 49 subjects were digested with Mnl I. This product contains an invariant Mnl I site at position 335 giving an invariant 61 bp fragment and a polymorphic fragment, 72 bp in the absence of site 368 or 33 and 39 base pairs if the Mnl I site at 368 is present. 9/49 subjects gave both the 72 bp and 33/39 bp products indicating that the Mnl I site at position 368 was lost from one allele and these subjects were heterozygous at position 375. The frequency of the A allele at 375 is thus 9/98.

Additional RFLPs generated by this variant are loss of an M.CviA IV and M.Sss I site.

This variant modifies a transcription factor binding site AP-2 CS4.

Variant Position 815

CMC analysis of fragment 1 produced cleavage products of approximately 230 bp and 750 bp in 2/49 subjects. Dye-primer sequence analysis of fragment 1 from 1 subject showing this pattern revealed a substitution of A for C at position 815. This was confirmed by sequencing 8 clones of fragment 1 from this subject. 4/8 had A at position 815 and 4/8 had C.

Substituting A for C at position 815 generates an Ava II site at 813.

PCR products from $LTC_4$ synthase position 417 to 1043 from 53 subjects were digested with Ava II. In 5/53 subjects an Ava II site at position 815 was created. These subjects were heterozygous at position 815. The frequency of the A allele was thus 5/106 alleles.

Additional RFLPs generated by this variant are loss of Aca I, CviK I, M.CviA IV, CviJ I and Hae III sites and gain of Asp697 I, VpaK11A I and Sin I sites.

This variant modifies a transcription factor binding site: AP-2 CS5.

Variant Position 1003

CMC analysis of fragment 1 produced a cleavage product of approximately 940 bp in 22/49 subjects. CMC analysis of fragment 2 (851–1824) produced a band of approximately 800 bp. Dye-primer sequence analysis of fragment 2 from 24 subjects showing this pattern revealed a substitution of C for A at position 1003. This was confirmed by sequencing 14 clones of fragment 1 from 2 subjects with the 940 bp cleavage product. 6/14 had C at position 1003 and 8/14 had A.

Substituting C for A at position 1003 generates an Ava II site at position 999. PCR products from $LTC_4$ synthase position 417 to 1043 from 53 subjects were digested with Ava II. In 26/53 subjects an Ava II site at position 1003 was created. One of these subjects was homozygous C/C at position 815 and 25 were heterozygous C/A. The frequency of the C allele was thus 27/106 alleles.

The 1003 C variant is not on the same chromosome as the 815 A variant.

Additional RFLPs generated by this variant are gain of sites for Bcr I, AhaB I, Asp697 I, VpaK11A I, Asu I, Fmu I, Sau96 I, Sin I, Nla IV, Asp I, Asp748 I, BsaC I, Dsa V, Eco1831 I, Hin2 I, Hpa II, Msp I, Bcn I, Nci I, ScrF I and M.Sss I.

This variant modifies the glucocorticoid receptor binding site GGGACA, (Chan et al., J. Biol. Chem. 266, 22634–22644, 1991).

Sanak et al. (1998), Lancet, 350, 1599, have reported an increased risk of aspirin induced asthma (AIA) being associated with this polymorphism (Sanak's position −444 is equivalent to our position 1003). AIA affects about 10% of adult asthmatics. Aspirin and other cyclo-oxygenase inhibitors cause release of LTs into airways, leading to an asthma attack. Clinical approaches to deal with AIA include pretreatment with anti-leukotriene drugs (Szczeklik (1997), Allergy, 52,613–9). Commentators have written approvingly of the clinical utility of detection of $LTC_4$ polymorphisms (Holgate (1998), Lancet, 351, 1300–1301, see last paragraph in particular).

Variant Position 2169

Dye-primer sequencing of fragment 6 (1503–2400) from 47 subjects demonstrated a substitution of T for C at position 2169 in 3 subjects.

Substituting T for C at position 2169 generates an Apa LI site at position 647.

Fragment 6 was digested with ApaL I. In 3/54 subjects an Apa LI site was created. These subjects were heterozygous for the RFLP, thus the frequency of the T allele at position 2169 is 3/108 alleles.

Additional RFLPs generated by this variant are loss of M.CviA IV, Bca I, Hinp I, Hinpl I, Cfo I, Hha I and M.Sss I sites and gain of Aaq I, Bkal125 I, BsaG I, CviR I, BsiHKA I, Bsp 1286 I, Hgi A I and Nsp II sites.

This variant disrupts an MREc-(3) site (Labbe et al., Nuc. Acid Res. 19,4225–4231 1991).

EXAMPLE 2

Detection of Variants 375, 815, 1003 and 2169 Using ARMS™

The following primers were used in ARMS™ PCR to distinguish allelic variants at positions 375, 815, 1003 and 2169 of the $LTC_4$ synthase gene.

| Allelic Variant Detected | Allele Specific Primer Sequence** | Constant Primer Sequence*** |
|---|---|---|
| 375 G | GGAGTTCTGGGTGTCTCCATC | GGTCAGTCTGGACTTTGCCAC |
| A | GGAGTTCTGGGTGTCTCCATT | |
| 815 C | TAGGGGTTCCATGCACAAGGG | TTGTTACCTTGAGGCAAGAGG |
| C | TAGGGGTTCCATGCACAATGG | |
| A | TAGGGGTTCCATGCACAAGGT | |
| A | TAGGGGTTCCATGCACAATGT | |
| 1003 A | CACCCACCTTATCTGTTCCCT | AGGCTGGCAGGCATGAGGTTT |
| C | CACCCACCTTATCTGTTCCCG | |
| A | GGAACAGCCTGGATGGGGTCA | TTCGTGCCCCTTCCTTGCCTA |
| C | GGAACAGCCTGGATGGGGTCC | |
| 2169 C | CAGACCAGTGCTGGCTGTACG | CTCCAGCTGCTCCTGCACTGA |
| T | CAGACCAGTGCTGGCTGTACA | |

**These primers are represented by SEQ ID NO: 10–21 respectively.
***These primers are represented by SEQ ID NO: 22–26 respectively.

Genomic DNA (50 ng) was amplified for 35 cycles with the above pairs of primers. The annealing temperatures were 62°, 60°, 64° and 60° for 375, 815, 1003 and 2169 respectively.

Homozygotes for the less common allele were only available for position 1003. The above primers and conditions would distinguish A/A, A/C and C/C genotypes at position 1003.

375 A/A homozygotes were not available so it could not be demonstrated that the G specific primer would not recognize A/A homozygotes but the A specific primer did not recognize G|G homozygotes. 815 A/A homozygotes were not available so it could not be demonstrated that the C specific primer would not recognize A/A homozygotes but the A specific primer did not recognize C/C homozygotes. 2169 T/T homozygotes were not available so it could not be demonstrated that the C specific primer would not recognize T/T homozygotes but the T specific primer did not recognise C/C homozygotes.

EXAMPLE 3

Polymorphism at Position 2742

Dye primer sequencing, as described in Example 1, of fragment 2180–2972 from 5 subjects demonstrated a substitution of T for C at position 2742 in 2 subjects. Template was prepared as described in Example 1 using the conditions set out below.

| Fragment | Forward Oligonucleotide | Reverse Oligonucleotide | Annealing Temperature | Time | % DMSO |
|---|---|---|---|---|---|
| 2180–2973 | 2180–2200 | 2953–2973 | 65° | 60 s | 10 |

This variant disrupts a RIPE3b site (Shieh and Tsai, J. Biol. Cbem. 266, 16708–16714, 1991).

What is claimed is:

1. A method for detection of at least one single nucleotide polymorphism (SNP) in a human $LTC_4$ synthase gene, which method comprises determining a nucleotide at one or more of positions 375, 815, 1003, 2169 and 2742 in the human $LTC_4$ synthase gene as defined by the positions in SEQ ID NO: 1, and thereby detecting absence or presence of at least one SNP.

2. A method according to claim 1 in which the single nucleotide polymorphism at position 375 is presence of G and/or A.

3. A method according to claim 1 in which the single nucleotide polymorphism at position 815 is presence of C and/or A.

4. A method according to claim 1 in which the single nucleotide polymorphism at position 1003 is presence of A and/or C.

5. A method according to claim 1 in which the single nucleotide polymorphism at position 2169 is presence of C and/or T.

6. A method according to claim 1 in which the single nucleotide polymorphism at position 2742 is presence of C and/or T.

7. A method according to any one of claims 1–6 in which the sequence is determined by a method selected from amplification refractory mutation system and restriction fragment length polymorphism.

8. An isolated and purified nucleic acid comprising the 5' untranslated region of the $LTC_4$ synthase gene comprising a polymorphism at one or more of positions 375, 815 and 1003 as defined by the positions in SEQ ID NO: 1 and in which there is an A at position 375, an A at position 815 and a C at position 1003.

9. An isolated and purified nucleic acid comprising the first intron of the $LTC_4$ synthase gene comprising a polymorphism at one or more of positions 2169 and 2742 as defined by the position in SEQ ID NO: 1 and in which there is a T at position 2169 and there is a T at position 2742.

10. An allele-specific nucleic acid primer of 17–35 nucleotides which specifically hybridizes to and detects a $LTC_4$ synthase gene polymorphism at one or more of positions 375, 815, 1003, 2169 and 2742 in the $LTC_4$ synthase gene as defined by the positions in SEQ ID NO: 1.

11. An isolated and purified allele-specific oligonucleotide probe of 17–35 nucleotides which specifically hybridizes to and detects a $LTC_4$ synthase gene polymorphism at one or more of positions 375, 815, 1003, 2169 and 2742 in the $LTC_4$ synthase gene as defined by the positions in SEQ ID NO: 1.

12. A diagnostic kit comprising a diagnostic primer as defined in claim 10 and/or an allele-specific oligonucleotide primer as defined in claim 11.

* * * * *